(12) United States Patent  
Radai et al.

(10) Patent No.: US 10,788,304 B2  
(45) Date of Patent: Sep. 29, 2020

(54) SYSTEM FOR AND A METHOD OF MEASURING A PATH LENGTH USING A HANDHELD ELECTRONIC DEVICE

(71) Applicant: MY SIZE ISRAEL 2014 LTD., Airport (IL)

(72) Inventors: Michal Miriam Radai, Ra'anana (IL); Meni Menashe Itzhak, Rosh Ha'ayin (IL)

(73) Assignee: My Size Israel 2014 Ltd., Airport City (IL)

( * ) Notice: Subject to any disclaimer, the term of this patent is extended or adjusted under 35 U.S.C. 154(b) by 340 days.

(21) Appl. No.: 15/548,260

(22) PCT Filed: Feb. 2, 2016

(86) PCT No.: PCT/IL2016/050114  
§ 371 (c)(1),  
(2) Date: Aug. 2, 2017

(87) PCT Pub. No.: WO2016/125151  
PCT Pub. Date: Aug. 11, 2016

(65) Prior Publication Data  
US 2018/0023937 A1 Jan. 25, 2018

(30) Foreign Application Priority Data  
Feb. 2, 2015 (IL) .......................................... 237055

(51) Int. Cl.  
*G01B 5/02* (2006.01)  
*A61B 5/107* (2006.01)  
(Continued)

(52) U.S. Cl.  
CPC .............. *G01B 5/02* (2013.01); *A61B 5/1072* (2013.01); *A61B 5/6898* (2013.01); *G01C 21/20* (2013.01); *A61B 2562/0219* (2013.01)

(58) Field of Classification Search  
CPC . G01B 5/02; A61B 2562/0219; A61B 5/1072; A61B 5/6898; G01C 21/20  
See application file for complete search history.

(56) References Cited

U.S. PATENT DOCUMENTS

| 5,541,730 A * | 7/1996 | Chaney | .............. | G01B 9/02004 356/482 |
| 7,916,302 B2 * | 3/2011 | Fellows | ............... | G01C 19/665 356/473 |

(Continued)

FOREIGN PATENT DOCUMENTS

| CN | 103383253 A | 11/2013 |
| DE | 4222373 | 1/1994 |

(Continued)

*Primary Examiner* — Elias Desta (57) ABSTRACT

The present disclosure provides a method of measuring a path length using a handheld electronic device comprising an acceleration sensor. The method comprises: sensing an acceleration of the handheld electronic device while the handheld electronic device is translated over the path, thereby obtaining an acceleration plot of the handheld device; and calculating the path length from the acceleration plot using an integration procedure. In some cases projection of a distance over a required measured path is used.

31 Claims, 6 Drawing Sheets

(51) Int. Cl.
*G01C 21/20* (2006.01)
*A61B 5/00* (2006.01)

(56) References Cited

U.S. PATENT DOCUMENTS

| | | | |
|---|---|---|---|
| 2002/0002863 A1 | 1/2002 | Slycke et al. | |
| 2007/0215413 A1 | 9/2007 | Tyni et al. | |
| 2011/0066395 A1* | 3/2011 | Judd | G01C 19/56 702/104 |
| 2013/0324857 A1* | 12/2013 | Kurillo | A61B 5/1127 600/476 |
| 2014/0100813 A1 | 4/2014 | Showering | |
| 2015/0027200 A1 | 1/2015 | Akiyama | |

FOREIGN PATENT DOCUMENTS

| | | |
|---|---|---|
| FR | 2 317 631 A1 | 2/1977 |
| JP | H08-114439 A | 5/1996 |
| JP | H09-33279 A | 2/1997 |
| JP | 2013-190265 A | 9/2013 |
| RU | 87540 | 11/1950 |
| WO | 2004/018971 | 3/2004 |
| WO | 2014/203433 A1 | 12/2014 |
| WO | 2014/203539 A1 | 12/2014 |

* cited by examiner

SYSTEM FOR AND A METHOD OF MEASURING A PATH LENGTH USING A HANDHELD ELECTRONIC DEVICE

TECHNOLOGICAL FIELD

The present disclosure relates generally to handheld electronic devices. More particularly, the present disclosure relates to a method of measuring a path length using one or more sensors integrated in a handheld electronic device and to a handheld electronic device adapted for implementing said method.

BACKGROUND

In the context of online commerce, dimensioning is a long standing issue for both online shoppers and online retail shops. Online shopping allows a user to view and purchase an item online, over the Internet, and in some examples, via a web browser on a phone, personal computer, television and/or other Internet connected device without trying the item on or without determining how well it will fit.

E-commerce, m-commerce and other forms of online shopping and commerce also allow a retailer, distributor, or another component of a supply chain for an item, to broaden their market, selling items to markets where sizing information may not necessarily be transferable, given different measurements or different average body sizes.

Consumers may not necessarily interact with a retailer online. In some examples, a consumer may search for an item via a search engine, a shopping search engine, and/or aggregators.

GENERAL DESCRIPTION

Mobile devices, such as smart phones, tablets, music players etc., are increasingly integrating accelerometers to detect motion. Such sensors are generally being used for applications such as gaming, screen rotation and power management.

The present disclosure relates to a method of measuring a path length using a handheld electronic device comprising an acceleration sensor. The presently disclosed method may be useful in the context of online commerce since it enables an online shopper to measure a part of the body and/or available clothing, using for example their smartphone.

In the present application, the following terms and their derivatives may be understood in light of the below explanations:

The term plot may be used to refer to a sequence of values associated with a time indication. The plot may be represented in two dimensions as a graph.

The term interval may refer to a set of contiguous elements of a sequence of ordered elements. For example, an acceleration plot may consist of a set of sampling points associated with time stamps and an interval may refer to a set of time stamps corresponding to contiguous sampling points of the acceleration plot.

The term path may refer to a linear path i.e. a path extending substantially along one path line. The path may be (slightly) curved and errors caused by a slight curve of the path line may be for example corrected by sensing acceleration components perpendicular to the path line. The path/path line may be supported by a supporting surface of an object. For example, the path may be supported by a body part or a plane surface. In some embodiments, friction between the handheld electronic device and the supporting surface may also cause errors which may be corrected. Intrinsic error may also be caused by the mobile hardware.

The term translation may be understood as referring to a linear movement of the handheld electronic device from a starting point to an ending point, the handheld electronic device being moved substantially in one direction parallel to the path line. In some embodiments, the handheld electronic device may be slid on the path line from the starting point to the ending point. In some embodiments, the handheld electronic device may be hovered over the path line. In some embodiments, the supporting surface may extend perpendicular to gravity.

In view of the nature of the translation movement it is understood that a sensed acceleration of interest may substantially be a linear acceleration as projected on the path line. In other words, the acceleration of interest may be a projection of the acceleration vector on the path line. Furthermore, the translation movement may be such that the handheld electronic device is stopped at the starting point and at the ending point. In some embodiments, the starting point and the ending point may be detected, for example through user input via a button command, a voice command, etc.

Therefore, the present disclosure provides a method of measuring a path length using a handheld electronic device comprising an acceleration sensor. The method comprises: sensing an acceleration of the handheld electronic device while the handheld electronic device is translated over the path, thereby obtaining an acceleration plot of the handheld device; computing a set of velocity plots by integrating the acceleration plot over a set of integration intervals, wherein the integration intervals have a decreasing span and exclude a growing initial portion of the acceleration plot; computing a set of distances by integrating the set of velocity plots; and estimating the path length based on the set of computed distances.

In some embodiments, an end point of each integration interval corresponds to the last sensed acceleration.

In some embodiments, a starting point of the integration interval of largest span is determined by analyzing the acceleration plot.

In some embodiments, analyzing the acceleration plot comprises detecting a major change of acceleration.

In some embodiments, analyzing the acceleration plot comprises detecting an acceleration sensor noise.

In some embodiments, a starting point of each subsequent integration interval after the integration interval of largest span corresponds to an acceleration sensed after the starting point of the integration interval of largest span.

In some embodiments, a starting point of the integration interval of largest span corresponds to the first sensed value.

In some embodiments, the starting point of each subsequent integration interval after the interval of largest span is defined recursively and corresponds to an acceleration sensed after the starting point of the preceding integration interval.

In some embodiments, the starting point of each subsequent integration interval after the interval of largest span is defined recursively and corresponds to an acceleration sensed immediately after the starting point of the preceding integration interval.

In some embodiments, estimating the path length is based on a statistical analysis of the set of computed distances.

In some embodiments, estimating the path length involves clustering techniques. In particular, estimating the path length may involve one dimension clustering.

In some embodiments, estimating the length comprises excluding irrelevant distances from the statistical analysis.

In some embodiments, estimating the length comprises: rounding each computed distance to the closest integer to obtain a set of rounded distances associated with the set of computed distances; determining the most frequent rounded distance among the rounded distances; determining a set of relevant distances consisting of the computed distances associated with rounded distances distant of less than a predetermined integer from the most frequent rounded distance; and performing the statistical analysis on the set of relevant distances.

In some embodiments, the statistical analysis comprises determining a median value.

In some embodiments, the method comprises correcting at least some velocity plots and computing the set of distances using the at least some corrected velocity plots.

In some embodiments, correcting at least some velocity plots is performed by subtracting a first degree polynomial function from said at least some velocity plots so that resulting corrected starting and ending sections of the at least some corrected velocity plots are substantially equal to zero. The term "substantially equal to zero" may be understood as "close to zero value" for example such that distances between zero and values of the ending and starting sections may be below a predetermined threshold.

In another aspect, the present disclosure provides one or more non-transitory computer-readable media storing computer-readable instructions that, when executed by a handheld electronic device translated over a path to be measured, cause the handheld electronic device to measure the path length by: sensing an acceleration of the handheld electronic device while the handheld electronic device is translated over the path, thereby obtaining an acceleration plot of the handheld device; computing a set of velocity plots by integrating the acceleration plot over a set of integration intervals, wherein the integration intervals have a decreasing span and exclude a growing initial portion of the acceleration plot; computing a set of distances by integrating the set of velocity plots; and estimating the path length based on the set of computed distances.

In another aspect, the present disclosure provides a handheld electronic device adapted for measuring a path length, the handheld electronic device comprising: an acceleration sensor configured for sensing an acceleration of the handheld electronic device; memory; and a processor communicatively coupled to the memory and the acceleration sensor, wherein the memory includes instructions for causing the processor to perform the steps of: sensing an acceleration of the handheld electronic device while the handheld electronic device is translated over the path, thereby obtaining an acceleration plot of the handheld device; computing a set of velocity plots by integrating the acceleration plot over a set of integration intervals, wherein the integration intervals have a decreasing span and exclude a growing initial portion of the acceleration plot; computing a set of distances by integrating the set of velocity plots; and estimating the path length based on the set of computed distances.

In another aspect, the present disclosure provides a computer program product adapted to perform the method previously described.

In another aspect, the present disclosure provides a measuring module for a handheld electronic device, the measuring module enabling to measure a path length and comprising: a user interface configured for receiving user input indicative of a starting and an ending of a translation movement of the handheld electronic device over the path; data receiver unit configured for obtaining from an acceleration sensor an acceleration plot of the handheld device, the acceleration plot being indicative of an acceleration of the handheld electronic device while the handheld electronic device is translated over the path; a data processing unit configured for: computing a set of velocity plots by integrating the acceleration plot over a set of integration intervals, wherein the integration intervals have a decreasing span and exclude a growing initial portion of the acceleration plot; computing a set of distances by integrating the set of velocity plots; and estimating the path length based on the set of computed distances; and an output unit configured for outputting the estimated path length to a user.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Described herein are some examples of systems and methods useful for measuring a path length.

In the following detailed description, numerous specific details are set forth in order to provide a thorough understanding of the subject matter. However, it will be understood by those skilled in the art that some examples of the subject matter may be practiced without these specific details. In other instances, well-known methods, procedures and components have not been described in detail so as not to obscure the description.

As used herein, the phrase "for example," "such as", "for instance" and variants thereof describe non-limiting examples of the subject matter.

Reference in the specification to "one example", "some examples", "another example", "other examples, "one instance", "some instances", "another instance", "other instances", "one case", "some cases", "another case", "other cases" or variants thereof means that a particular described feature, structure or characteristic is included in at least one example of the subject matter, but the appearance of the same term does not necessarily refer to the same example.

It should be appreciated that certain features, structures and/or characteristics disclosed herein, which are, for clarity, described in the context of separate examples, may also be provided in combination in a single example. Conversely, various features, structures and/or characteristics disclosed herein, which are, for brevity, described in the context of a single example, may also be provided separately or in any suitable sub-combination.

Unless specifically stated otherwise, as apparent from the following discussions, it is appreciated that throughout the specification discussions utilizing terms such as "generating", "determining", "providing", "receiving", "using", "transmitting", "performing", "analyzing", "computing", "estimating" or the like, may refer to the action(s) and/or process(es) of any combination of software, hardware and/or firmware. For example, these terms may refer in some cases to the action(s) and/or process(es) of a programmable machine, that manipulates and/or transforms data represented as physical, such as electronic quantities, within the programmable machine's registers and/or memories into other data similarly represented as physical quantities within the programmable machine's memories, registers and/or other such information storage, transmission and/or display element(s).

Figure 1:
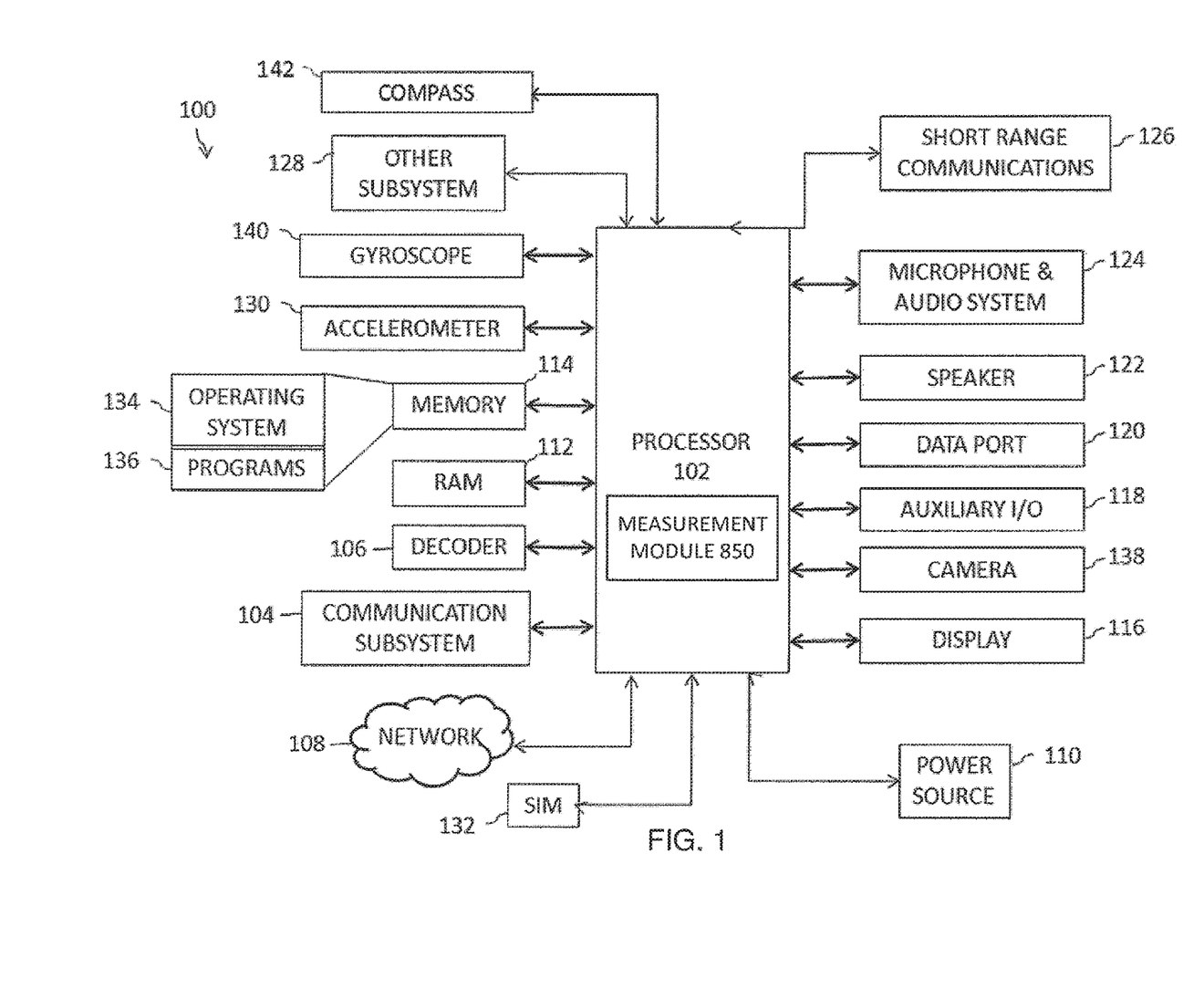
FIG. 1 is a functional diagram illustrating a handheld electronic device according to embodiments of the present disclosure.

FIG. 1 depicts a high-level functional block diagram of an electronic assembly 100 for operating a handheld electronic device according to the present disclosure. Electronic assembly 100 can include multiple components, such as processor 102, which can control the overall operation of the handheld electronic device. In some embodiments, communication functions provided by the handheld electronic device can include voice, data, and command communications, which may be implemented by communication subsystem 104. Communication subsystem 104 can be used to initiate and support an active voice call or data communication session. Communication subsystem 104 can include various combinations of hardware, software, and firmware to perform various designated functions. The software can be functionally or conceptually divided into software modules. Software in one module may share or call upon functions in other modules.

Data received by the handheld electronic device can be processed, including decompressed and decrypted, by decoder 106. Communication subsystem 104 can receive messages from, and send messages to, wireless network 108. Communication subsystem 104 can help initiate and operate an active call, wherein the handheld electronic device is in a real-time voice communication session. Wireless network 108 may be any type of wireless network, including, but not limited to, a cellular network, a wireless data network, a wireless voice network, and a network that supports both voice and data communications. Wireless network 108 can use a variety of formats or protocols, such as those specified by standards including Global System for Mobile Communications (GSM), Code division multiples access (CDMA), wireless Ethernet (Institute of Electrical and Electronics Engineers standard 802.11), Wi-Fi, and other similar standards and wireless networking protocols.

Power source 110 can provide power to operate or charge the handheld electronic device, and can be implemented with one or more rechargeable batteries, or a port to an external power supply, wherein such power supply provides the appropriate power to all components of electronic assembly 100.

Processor 102 can interact with other components, such as random access memory (RAM) 112, memory 114, display 116, auxiliary input/output (I/O) subsystem 118, data port 120, speaker 122, microphone and audio system 124, short-range communications subsystem 126, and other subsystems 128. A user can enter data and operate functions of the handheld electronic device with a data input device coupled to processor 102. Data input devices can include buttons or a keypad, or, in some embodiments, a graphical user interface produced on display 116, which can use touches and gestures detected by a touch-sensitive overlay on display 116. Processor 102 can interact with the keypad and/or the touch-sensitive overlay via an electronic controller (represented in FIG. 3 by the element other subsystems 128). As part of the user interface, information, such as text, characters, symbols, images, icons, and other items that may be displayed or rendered on the handheld electronic device, can be displayed on display 116.

To identify and authenticate a subscriber for obtaining access to wireless network 108, the handheld electronic device can use a subscriber identity module (SIM) card 132. Alternatively, user identification information can be programmed into memory 114.

A received signal, such as a text message, an e-mail message, or web page download can be processed by communication subsystem 104 and input to processor 102. Processor 102 can process the received signal for output to the display 116 and/or to the auxiliary I/O subsystem 118. A wireless device user may generate data items, for example e-mail messages containing a photograph, which may be transmitted over wireless network 108 through communication subsystem 104. For voice communications, the overall operation of the handheld electronic device can be similar.

Speaker 122 can be used to output audible information converted from electrical signals, and microphone and audio system 124 can be used to convert audible information into electrical signals for processing.

Camera subsystem 138 can include many hardware, software, and firmware modules that are needed to capture image data (e.g., visual data). Examples of image data include still photographs, and video frames included in the moving images of a video data file. For example, camera subsystem 138 can include lens 140, image sensor 142, and lens position controller 144.

Processor 102 can interact with one or more accelerometers 130 (also referred to as acceleration sensor(s)), which may be used to detect a direction of gravitational forces and user-input acceleration forces. The processor 102 may generally be operable to couple with the one or more accelerometers 130 to enable estimating a path length according to the method described herein. The one or more accelerometers 130 are each operable to measure an acceleration and generate an acceleration measurement corresponding to the measured acceleration. The acceleration measurement may be embodied as a signal operable to be utilized by the processor 102. In some embodiments, one or more of the accelerometers 130 may be operable to output an analog signal corresponding to an acceleration measurement. For instance, each accelerometer 130 may output an analog voltage signal that is proportional to measured accelerations. In some embodiments, the one or more accelerometers may include any digital and analog components operable to generate a signal corresponding to a measured acceleration. The one or more accelerometers 130 may be any of a spring mass device, a servo device, a strain gauge, a resonance device, and the like. In some embodiments, the one or more accelerometers 130 may include at least three accelerometers adapted to measure accelerations in three perpendicular directions. In some embodiments, a gyroscope 140 and/or a compass 142 may further be integrated in the handheld electronic device. The gyroscope, compass and accelerometers 130 may be coupled so as to enable sensor fusion. It is noted that the term sensing and its derivatives may refer in the present disclosure to the action of reading an output from the accelerometers 130.

The handheld electronic device can include operating system 134 and software programs 136 which can both be executed by processor 102. Operating system 134 and software programs 136 can be stored in a persistent, updatable format, such as memory 114. Additional applications or programs can be loaded onto the handheld electronic device through wireless network 108, auxiliary I/O subsystem 118, data port 120, short-range communications subsystem 126, or any other subsystem 128 suitable for transferring program files. Software programs 136 can include software modules such as a module for measuring a path length which may be responsible for implementing the method of estimating a path length herein disclosed. Software programs 136 may also include a Graphical User Interface (GUI) for interacting with a user and the module for estimating a path length. Each of these software modules can call upon various hardware and software resources within the handheld electronic device to execute a function. Additionally, functions described in the present disclosure can be implemented in various portions of electronic assembly 100, whether such portions be software modules, or specialized hardware and firmware modules. In many instances, it may be possible to implement the same function in more than one portion of electronic assembly 100.

Figure 8:
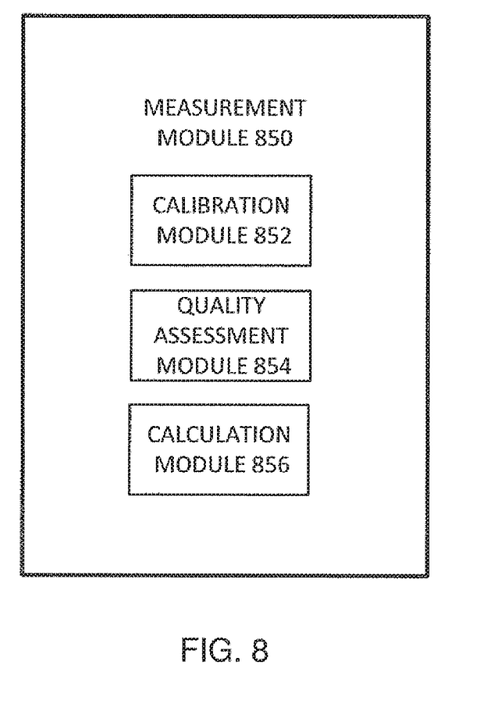
FIG. 8 is a functional block diagram illustrating the measurement module of the handheld electronic device of FIG. 1, according to embodiments of the present disclosure.

According to a teaching disclosed herein the handheld electronic device can comprise a measurement module 850.

Reference is now made to FIG. 8. FIG. 8 is a functional block diagram illustrating measurement module 850 of the handheld electronic device of FIG. 1, according to an example of the presently disclosed subject matter. Measurement module 850 is configured to perform the measurement process herein disclosed. Measurement module 850 can further comprise a calibration module 852; a quality assessment module 854; and a calculation module 856.

Calibration module 852 is configured to perform the calibrations as disclosed herein. Quality assessment module 854 is configured to perform the quality assessments as disclosed herein. Calculation module 856 is configured to the calculation of a path length as disclosed herein. Measurement module 850, calibration module 852, quality assessment module 854, and calculation module 856 may be integrated as part of a processor (e.g., processor 102 described above with reference to FIG. 1) and/or memory. Alternatively, measurement module 850, calibration module 852, quality assessment module 854, and calculation module 856 may be external to and operatively connected to a processor. The modules in FIG. 8 may be centralized in one location or dispersed over more than one location. A more detailed description of the various operations of the various modules is provided below The handheld electronic device and measuring module 850 are both computerized devices comprising or otherwise operatively connected to at least one computer processing unit configured for executing various operations as described below. The terms "processing unit", "computer", "processing device", or variation thereof should be expansively construed to cover any kind of electronic device with data processing capabilities, including, by way of non-limiting example, a personal computer, a server, a computing system, a communication device, a processor (e.g. digital signal processor (DSP), a microcontroller, a field programmable gate array (FPGA), an application specific integrated circuit (ASIC), etc.), any other electronic computing device, and\or any combination thereof. In some examples the handheld electronic device may be a smartphone, computer tablet or smart-watch In embodiments of the presently disclosed subject matter, fewer, more and/or different stages than those shown in FIGS. 2, 6 and 7 may be executed. In embodiments of the presently disclosed subject matter one or more stages illustrated FIGS. 2, 6 and 7 may be executed in a different order and/or one or more groups of stages may be executed simultaneously.

Figure 2:
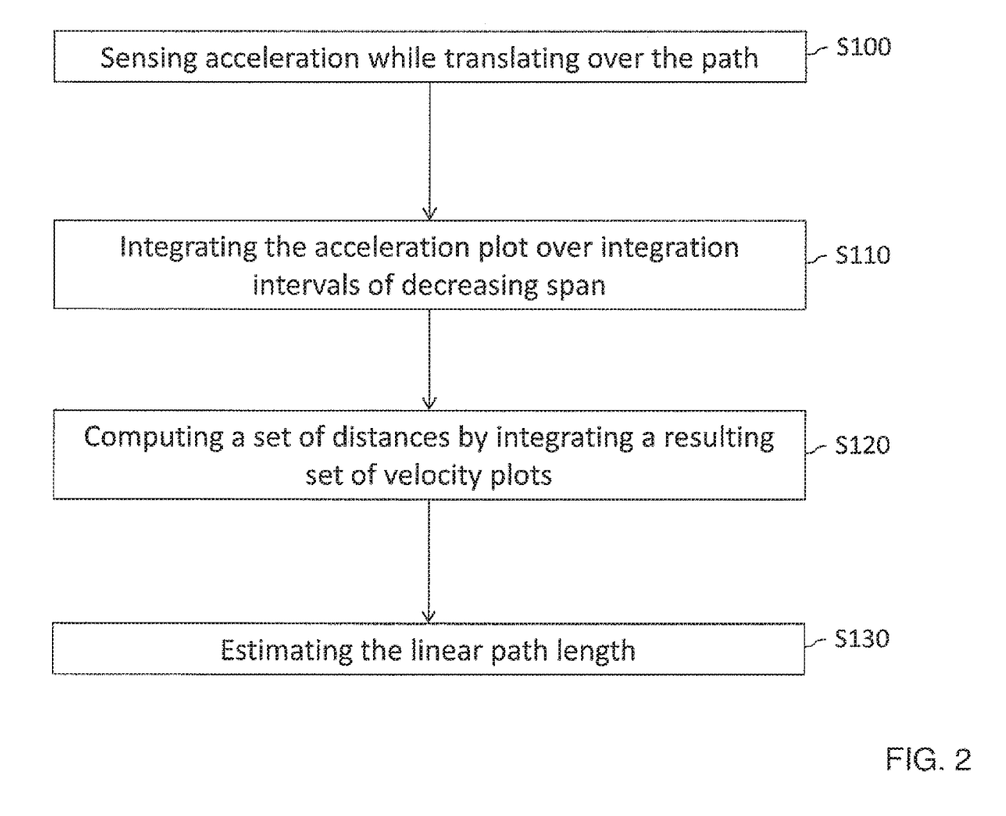
FIG. 2 is a flow chart illustrating steps of a method of estimating a path length according to embodiments of the present disclosure.
Figure 3:
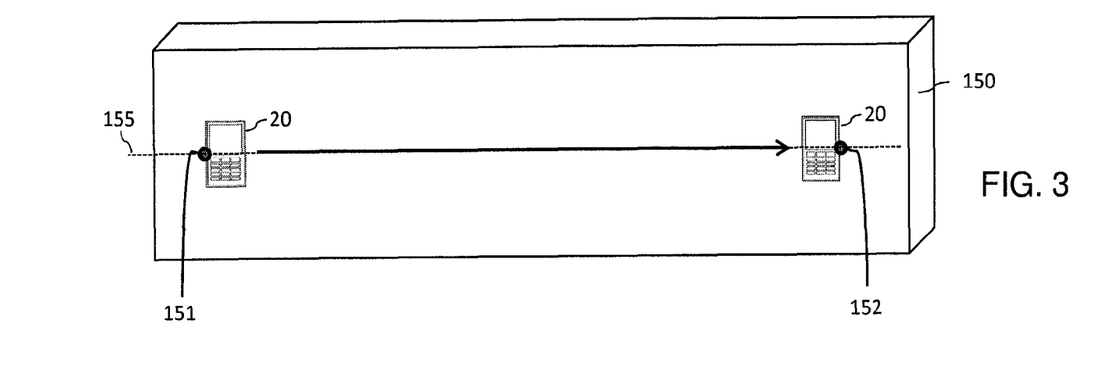
FIG. 3 illustrates a translation movement of the handheld electronic device in a method of estimating a path length according to embodiments of the present disclosure.

FIG. 2 illustrates, generally, steps of a method of measuring a path length using an integration procedure according to embodiments of the present disclosure. The method of measuring a path length may be implemented on a handheld electronic device as described hereinabove. In a step S100, an acceleration of the handheld electronic device may be sensed while the handheld electronic device is translated over the path to be measured. The translation movement may be performed according to a path line. The sensed acceleration may refer to a linear acceleration as projected on the path line. As illustrated in FIG. 3, the path may be supported by path line 155 on a surface of an object 150. In some embodiments, a supporting surface of the path line may extend perpendicular to gravity. The handheld electronic device 20 may be slid on the object's surface from a starting point 151 to an ending point 152 of the path line 155. There may be different starting position configurations, depending on the position of the handheld electronic device at the starting and ending points 151, 152. In some embodiments, in the starting position, an edge of the handheld electronic device 20 may be perpendicular to the path direction in which the path to be measured extends. In some embodiments, a starting configuration may be such that the handheld electronic device 20 covers a portion of the path to be measured (as shown in FIG. 3). In some embodiments (not shown), a starting configuration may be such that the handheld electronic device 20 does not cover the path to be measured. The handheld electronic device 20 may be configured so as to be informed of the starting position configuration to properly calculate the path length, for example through a menu in a GUI. This enables to compensate for the starting configuration and in particular for the dimensions of the handheld electronic device in the length measurement.

Step S100 may thereby provide an acceleration plot comprising a sequence of time stamped sampling points indicative of acceleration of the handheld electronic device between the starting point 151 and the ending point 152. A timer may be provided and coupled with the acceleration sensor so that acceleration is sensed by the acceleration sensor(s) when the timer is activated. In some embodiments, the timer may be activated by the user at the starting point 151, for example by pressing an activation button, and be deactivated at the ending point 152, for example by releasing the activation button. In some embodiments, the translation movement may be started upon lapsing of a predetermined period after the timer has been activated. In some embodiments, the timer may be stopped after a predetermined period lapsed after the end of the translation movement. This enables to analyze the sensed acceleration without movement to detect an intrinsic noise of the acceleration sensor prior to the actual translation movement. As explained above, the acceleration of interest may be a projection of the acceleration along the path line. This may be performed using positional information provided by the handheld electronic device.

Figure 4:
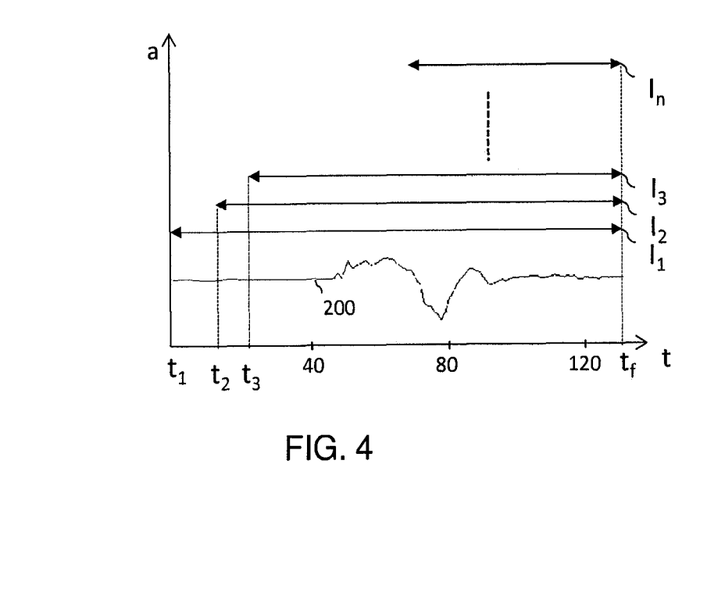
FIG. 4 is an exemplary acceleration plot and illustrates a set of integration intervals according to embodiments of the present disclosure.

In a step S110, the acceleration plot may be integrated over a set of integration intervals. The integration intervals may be of decreasing span and exclude a growing initial portion of the acceleration plot. In other words, the integration intervals can be ordered from a first integration interval of largest span, to a last integration interval of smallest span, the integration intervals gradually exclude a beginning phase of the acceleration plot. Therefore, a set of integrals of the acceleration plot are computed over time intervals of decreasing span and increasingly excluding sampling points of an initial portion of the acceleration plot. In some embodiments, the integration intervals are defined recursively by the first integration interval (which may in some embodiments correspond to all the sampling points of the acceleration plot) and each subsequent integration interval being obtained by removing the earliest sampling point of the preceding integration interval. In some embodiments, a starting point of the first integration interval may be determined based on detecting an abrupt variation in the acceleration plot. In one embodiment, the number of integration intervals may amount for example to half the number of sampling points. The Applicant has found that this enables to provide satisfactory accuracy while limiting the computational load. FIG. 4 illustrates an exemplary embodiment in which a set of integration intervals $I_1, I_2, I_3, \ldots, I_n$ are represented above a measured acceleration plot 200. It is noted that the integration intervals are hereby arbitrarily indexed based on their span for facilitating the description. However, this is not deemed to limit the scope of the present disclosure. As can be seen $I_1$ includes all the sampling points of the acceleration plot 200 i.e. extends from a time $t_1$ at which the sensing of the acceleration begins and a time $t_f$ at which the sensing of the acceleration ends. Further, $I_2$ has a span shorter than $I_1$ and excludes an initial portion of the acceleration plot i.e. extends from a time $t_2$ later than $t_1$ until the time $t_f$ at which sensing stops. Similarly, $I_3$ has a span shorter than $I_2$ and excludes a larger initial portion of the acceleration plot than $I_2$ because $I_3$ extends from a time $t_3$ later than $t_2$ and until the time $t_f$ at which sensing stops. Step S110 may therefore provide a set of velocity plots computed by integrating the sensed acceleration over the set of integration intervals.

Figure 5:
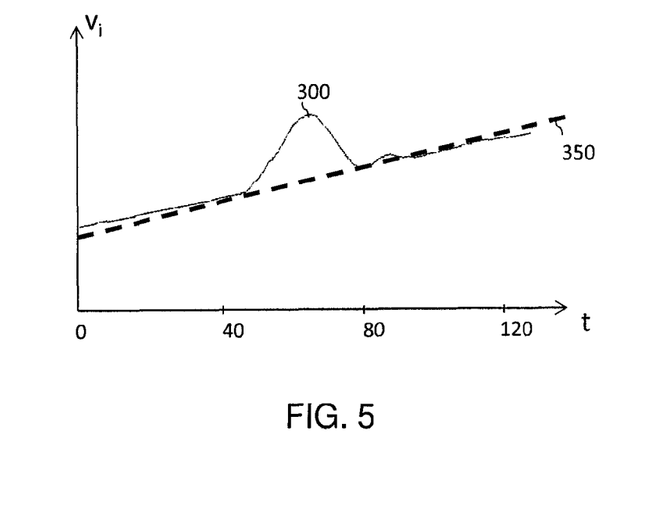
FIG. 5 is an exemplary velocity plot and illustrates a first degree correction according to embodiments of the present disclosure.

In a step S120, a set of distances may be computed by integrating the set of velocity plots derived from step S110. In some embodiments, step S120 may comprise correcting a linear bias in at least some of the velocity plots and integrating the corrected velocity plots. In some embodiments, the linear bias may for example be corrected by approximating said at least some velocity plots using least square techniques and by subtracting the resulting approximated linear functions from the corresponding velocity plots. FIG. 5 illustrates a velocity plot 300 and an approximated linear function 350 which may be calculated by least square techniques, as explained above. Also as explained above, subtracting the approximated linear function 350 from the velocity plot 300 may provide a corrected velocity plot. The corrected velocity plot may be used instead of the velocity plot in step S120 for computing the corresponding distance by integration. In some embodiments, correcting at least some velocity plots may be performed by subtracting a first degree polynomial function, so that the starting and ending sections of the at least some corrected velocity plots are substantially equal to zero (i.e. a distance between the values of the starting and ending sections and the zero axis is below a predetermined threshold).

In a step S130, a path length may be estimated based on the set of computed distances derived from step S120. Estimating the path length may involve statistical analysis of the set of computed distances. For example, the statistical analysis may include calculating a median value on at least some (or all) of the computed distances derived from step S120. In some embodiments, the statistical analysis may involve clustering techniques, for example one-dimensional clustering of the computed distances and searching for a center of the one-dimensional cluster. In some embodiments, three axes acceleration data may be sensed. In these embodiments, the computed distances may comprise three components and the statistical analysis may involve multi-dimensional clustering. For example, in the one-dimensional approach, estimating the length may comprise rounding each computed distance to the closest integer to obtain a set of rounded distances associated with the set of computed distances; determining the most frequent rounded distance among the rounded distances, for example by building a bar histogram, and determining a set of relevant distances consisting of the computed distances associated with rounded distances distant of less than a predetermined integer from the most frequent rounded distance. For example, the predetermined integer may be equal to 1, 2 or 3 cm. Thereafter, the statistical analysis may be performed on the set of relevant distances.

Figure 6:
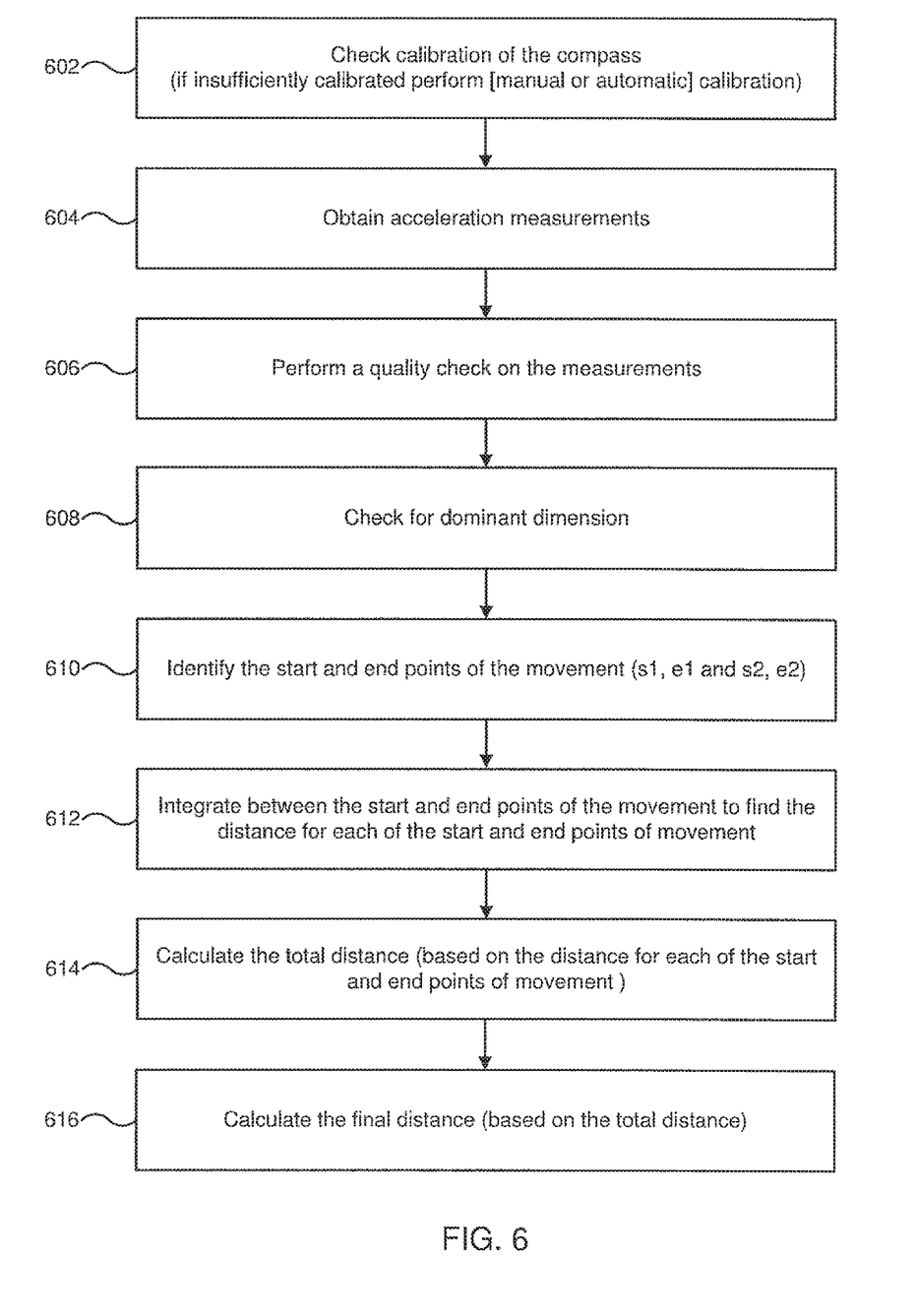
FIG. 6 is a flow chart illustrating a method of calculating a path length, according to embodiments of the present disclosure.

Reference is now made to FIG. 6. FIG. 6 is a flowchart illustrating operations carried out for calculating a distance of a path length using an integration procedure, according to examples of the presently disclosed subject matter. Operations described with reference to FIG. 6 may be executed by handheld electronic device 20 described above with reference to FIGS. 1 and 3.

In block 602 the compass of the handheld electronic device is checked for a True North or Magnetic North calibration. According to one example, a magnet or a magnetometer together with a gyroscope inside handheld electronic device 20 is used as a compass to determine the orientation of handheld electronic device 20 relative to the ground.

A preliminary calibration procedure may be carried out (e.g., by calibration module 852) to check the compass in handheld electronic device 20 and determine whether the compass is sufficiently calibrated to True North or Magnetic North. In addition to determining the current level of calibration, during the preliminary calibration procedure it can be checked when the previous calibration was performed on handheld electronic device 20. If the calibration level is insufficient and/or the time since the previous calibration was performed is greater than a certain predefined time period, then the user can be requested to perform a manual calibration. The user can be prompted and instructed how to perform the calibration. In certain examples handheld electronic device 20 can be automatically calibrated to set the compass on handheld electronic device 20 to True North or Magnetic North using calibration module 852 which is configured to communicate with the compass controls of handheld electronic device 20.

In block 604, acceleration measurements of handheld electronic device 20 are obtained for two dimensions (X, Y) while handheld electronic device 20 is traversed or translated over path 155 (from point 151 to point 152). According to some examples, acceleration sensors 130 and gyroscope 140 can be configured to obtain the measurements, and measurement module 850 can be configured to receive the measurements from the sensors. Handheld electronic device 20 can receive user input indicative of a starting and an ending of a traversing or translating movement of handheld electronic device 20 over path 155 from user input 128.

Block 604 may thereby provide two acceleration plots (Xacc, Yacc), each acceleration plot comprising a sequence of time stamped sampling points indicative of acceleration of handheld electronic device 20 between starting point 151 and ending point 152 for each of the two dimensions (X, Y).

In addition to measuring the X, Y values of acceleration of the movement (Xacc, Yacc), the sensor(s), e.g., the compass/a magnetometer, can also sense the acceleration movement due to gravity. New X, Y values of acceleration (Xacc, Yacc) may be calculated based on the acceleration movement due to gravity, e.g., in a case where the path is not parallel to the ground.

In block 604, additional calibration may optionally be performed on the X, Y, values of acceleration. In addition to compensating the X, Y values of acceleration for the affect of gravity, the X, Y values of acceleration may be normalized Hereinafter, the term compensated will refer to the values after the affect of gravity has been removed and normalization has been done. According to some examples, calibration module 852 can be configured to carry out this calibration.

Optionally, in block 606, a quality check may also be performed. For the X, Y values of acceleration (Xacc, Yacc) the X, Y values of velocity are calculated by performing integration on the X, Y values of acceleration (Xacc, Yacc). The maximum velocity value is calculated using the maximum values of the total velocity. The maximum velocity value is used as an indication of quality measure. In some examples the maximum velocity value may be used as threshold for quality measure. Accordingly, in such a case the user may be prompted and instructed to perform the measurement process again from the beginning and at a higher speed. According to some examples, quality assessment module 854 can be configured to perform this quality check.

Optionally, in block 608 a check may be performed (e.g., by calculation module 856) to see if one of the dimensions (X or Y) is defined as a dominant dimension. The ratio between the maximum values of the X, Y values of velocity may be checked compared to a certain threshold. For example if one of the maximum values of the X, Y values of velocity (MaxXvel or MaxYvel) is a predefined amount greater than the other maximum value (MaxYvel or MaxXvel) than that dimension (X or Y) may be defined as the dominant dimension. If one of the dimensions (X or Y) are defined as a dominant dimension than one or more of the following steps may be performed only on the dominant dimension (X or Y), or may be omitted. If neither of the dimensions are defined as the dominant dimension then the following steps may be performed for both dimensions (X and Y). The following steps describe the case that neither of the dimensions are defined as the dominant dimension.

In block 610, the start and end points of the movement are identified for both dimensions X, Y. According to some examples, calculation module 856 can identify the start and end points of movement. In certain examples, identifying the start and end points of the movement (s1, e1 and s2, e2) is done using different weights. For this purpose various types of weights can be used including for example: standard deviation or slope.

Figure 7:
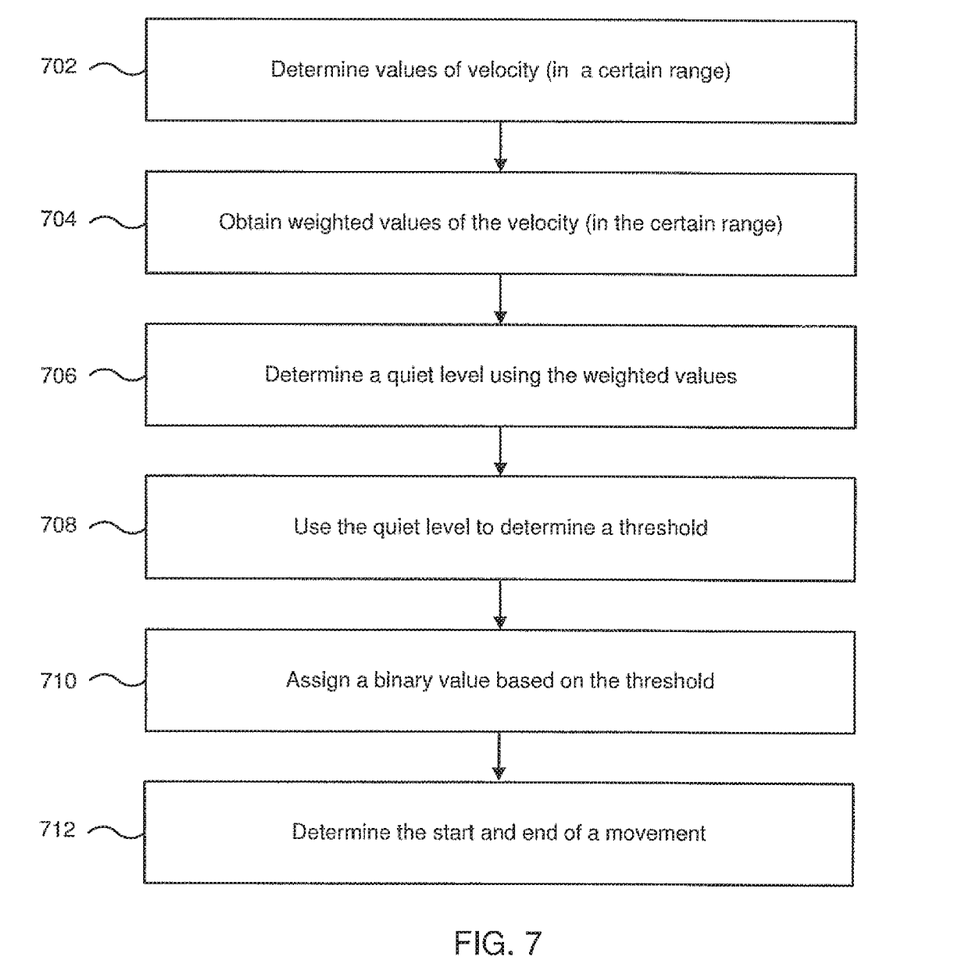
FIG. 7 is a flow chart illustrating a method of identifying the start and end points of the movement, according to embodiments of the present disclosure.

Reference is now made to FIG. 7, description of FIG. 6 is continued below. FIG. 7 is a flow chart illustrating a method of identifying the start and end points of the movement for both dimensions X, Y (which may be part of block 610). In block 702, according to some examples, the compensated absolute X, Y values of velocity (Xvel, Yvel), in a certain range are determined.

In block 704, a weighted value of velocity is obtained. In some examples, a sliding standard deviation window of a predetermined time period is used by calculation module 856 on the X, Y values of velocity (Xvel, Yvel) to calculate the standard deviation (Std). The standard deviation window calculates the difference between the samples. Where the changes are sharp (i.e., where the derivative is high) the result will be relatively high values. The standard deviation is used to emphasize and de-emphasize certain ranges of the velocity plot. In some examples, the weights are used to highlight low values that are near zero, since typically most of the measurement is in those areas. Alternatively, other weights such as slope calculation may be used.

In block 706, an average window of a predefined time period, equal to or shorter than a predefined period of time that the user is guided to wait before measurement, is used (e.g., by calculation module 856) on the weighted values derived in block 704 to determine a quiet level.

In block 708, a certain percentage above or below the quiet level is determined (e.g., by calculation module 856) as a threshold, e.g., defined as a predefined percentage above the quiet level.

In block 710, a binary value (0 or 1) is assigned (e.g., by calculation module 856) to the X, Y values of velocity (Xvel, Yvel) based on the threshold derived in block 708. If the given value is below the threshold it is assigned a 0 value, and if the given value is above the threshold it is assigned a 1 value. The result is a vector for each dimension X, Y with one or more rectangular functions.

In block 712, the time of the start and end of the widest rectangular function for each dimension X, Y is determined (e.g., by calculation module 856) as the start and end points of the movement (s1, e1). In some cases there will be more than one rectangular shape resulting in more than one pair of potential start and end points. In this case all the pairs are examined and one or more widest pairs may be determined as the start and end points of the movement. For example, in a case where two widest pairs are determined there will be two sets of start and end points of the movement (s1, e1 and s2, e2). In addition, sanity checks may be performed (e.g., by quality assessment module 854) on each of the pairs to see if that pair even needs to be considered at all. The time of the start and end of the determined widest pair(s) will be applied to the compensated X, Y values of velocity (Xvel, Yvel). The area of the X, Y values of velocity (Xvel, Yvel) between the determined start and end points is the length for that dimension X, Y. The following steps describe the case where there was more than one rectangular function.

Returning now to FIG. 6, at block 612, the area between the determined start and end points of the movement derived in block 610 is integrated for each of the dimensions X, Y to calculate the length of that dimension (e.g., distX1, distX2, and distY1, distY2). According to some examples, calculation module 856 can be configured to integrate these areas and to calculate these lengths.

The start and end points of the movement for each of the two dimensions X, Y derived in block 610 are applied (e.g., by calculation module 856) to the (X, Y values of velocity Xvel, Yvel for the) appropriate, respective one of each of the two dimensions X, Y. The normalized X, Y values of velocity (Xvel, Yvel) are integrated (e.g., by calculation module 856) between the start and end points of the movement (between s1 and e1 and between s2 and e2) to calculate the lengths for each dimension (distX1, distX2, and distY1, distY2).

In block 614, the total length for each dimension X, Y is calculated (e.g., by calculation module 856) based on the calculated distances for each start and end point of the movement derived in block 612.

In block 616, a final length based on the two lengths (totaldistX, totaldistY) derived in block 614 is calculated. In the previous procedure two scalar numbers, the length for X and the length for Y (totaldistX, totaldistY) were determined. In some examples, the procedure of calculating a final length based on the two lengths is done (e.g., by calculation module 856) using a Pythagoras equation on the calculated distances for each dimension X, Y to calculate the square root of totaldistX^2+totaldistY^2 to calculate the final length (Final Total). According to some examples, calculation module 856 can be configured to perform this calculation, display 116 can be configured to display the results to a user, memory 114 can be configured to store the results, and communication subsystem 104 can be configured to transmit the results to another computer processing device, such as a server.

In cases where there is a dominant dimension, the total length of the dominant dimension derived in block 614 may be the final length (there is no need for further calculation in step 616).

In cases where there is only one rectangular function, the lengths for each dimension (distX1, and distY1) derived in block 612 may be the total lengths for each dimension X, Y (totaldistX, and totaldistY) (there is no need for step 614, and the process may go from step 612 to step 616).

In some cases, e.g., where the measurement is done in more than one dimension, projection of a distance over a required measured path is used.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It will be appreciated that the embodiments described above are cited by way of example, and various features thereof and combinations of these features can be varied and modified.

While various embodiments have been shown and described, it will be understood that there is no intent to limit the invention by such disclosure, but rather, it is intended to cover all modifications and alternate constructions falling within the scope of the invention, as defined in the appended claims.

It will also be understood that the system according to the presently disclosed subject matter can be implemented, at least partly, as a suitably programmed computer. Likewise, the presently disclosed subject matter contemplates a computer program being readable by a computer for executing the disclosed method. The presently disclosed subject matter further contemplates a machine-readable memory tangibly embodying a program of instructions executable by the machine for executing the disclosed method.

The invention claimed is:

1. A method of measuring a path length using a handheld electronic device comprising a plurality of acceleration sensors, the method comprising, using a processor for:
   sensing an acceleration of the handheld electronic device for a first dimension and an acceleration of the handheld electronic device for a second dimension while the handheld electronic device is translated over the path, thereby obtaining a first acceleration plot of the handheld device for the first dimension and a second acceleration plot of the handheld device for the second dimension;
   calculating a first path length from the first acceleration plot using a first integration procedure;
   calculating a second path length from the second acceleration plot using a second integration procedure, wherein said first integration procedure or second integration procedure comprising:
      (i) identifying a start point of the movement and an end point of the movement; and
      (ii) integrating between the start point of the movement and the end point of the movement, to find the path length; and
   calculating a final path length based on the first path length and the second path length.

2. The method according to claim 1, said first or second integration procedure comprising:
   computing a set of velocity plots by integrating the acceleration plot over a set of integration intervals, wherein the integration intervals have a decreasing span and exclude a growing initial portion of the acceleration plot;
   computing a set of distances by integrating the set of velocity plots; and
   estimating the path length based on the set of computed distances.

3. The method according to claim 2, wherein an end point of each integration interval corresponds to the last sensed acceleration.

4. The method according to claim 2, wherein a starting point of the integration interval of largest span is determined by analyzing the acceleration plot.

5. The method according to claim 1, comprising analyzing the acceleration plot to detect a major change of acceleration.

6. The method according to claim 1, comprising analyzing the acceleration plot to detect an acceleration sensor noise.

7. The method according to claim 2, wherein a starting point of each subsequent integration interval after the integration interval of largest span corresponds to an acceleration sensed after the starting point of the integration interval of largest span.

8. The method according to claim 2, wherein a starting point of the integration interval of largest span corresponds to the first sensed value.

9. The method according to claim 2, wherein calculating the path length is based on a statistical analysis of the computed distance.

10. The method according to claim 2, comprising correcting at least some velocity plots and computing the set of distances using the at least some corrected velocity plots.

11. The method according to claim 1, comprising identifying the start and end point of the movement using at least one type of weight type.

12. The method according to claim 1, comprising calculating a maximum velocity and using the maximum velocity for an indication of quality measurement.

13. The method according to claim 1, comprising checking for a dominant dimension.

14. The method according to claim 1, comprising projecting movement of a distance over a required measured path.

15. The method according to claim 1, comprising measuring orientation with the help of a gyroscope sensor.

16. The method according to claim 15, comprising calibrating the acceleration measurements to compensate for the orientation potential inaccuracy.

17. The method according to claim 1, comprising measuring acceleration with the help of an acceleration sensor.

18. The method according to claim 1, comprising calibrating the handheld electronic device to True North or Magnetic North.

19. The method according to claim 1, wherein said procedure of obtaining acceleration measurements of the handheld electronic device further comprising receiving user input indicative of a starting and an ending of a traversing movement of the handheld electronic device over the path.

20. The method according to claim 1, wherein said handheld electronic device is a smart-phone.

21. A non-transitory computer-readable media storing computer-readable instructions that, when executed by a handheld electronic device translated over a path to be measured, cause the handheld electronic device to measure the path length by:
   sensing an acceleration of the handheld electronic device for a first dimension and an acceleration of the handheld electronic device for a second dimension while the handheld electronic device is translated over the path, thereby obtaining a first acceleration plot of the handheld device for the first dimension and a second acceleration plot of the handheld device for the second dimension;
   calculating a first path length from the first acceleration plot using a first integration procedure;
   calculating a second path length from the second acceleration plot using a second integration procedure, wherein said first integration procedure or second integration procedure comprising:
      (i) identifying a start point of the movement and an end point of the movement; and
      (ii) integrating between the start point of the movement and the end point of the movement, to find the path length; and
   calculating a final path length based on the first path length and the second path length.

22. The non-transitory computer-readable media storing computer-readable instructions of claim 21, said first or second integration procedure comprising:
   computing a set of velocity plots by integrating the acceleration plot over a set of integration intervals, wherein the integration intervals have a decreasing span and exclude a growing initial portion of the acceleration plot;
   computing a set of distances by integrating the set of velocity plots; and
   estimating the path length based on the set of computed distances.

23. A handheld electronic device configured to measure a path length, the handheld electronic device comprising:
   a first acceleration sensor configured to sense an acceleration of the handheld electronic device for a first dimension;
   a second acceleration sensor configured to sense an acceleration of the handheld electronic device for a second dimension;
   computer memory; and
   a processor operatively coupled to the memory and to the acceleration sensor, wherein the memory includes instructions for causing the processor to:
      sense an acceleration of the handheld electronic device for the first dimension and an acceleration of the handheld electronic device for the second dimension while the handheld electronic device is translated over the path, thereby obtaining a first acceleration plot of the handheld device for the first dimension and a second acceleration plot of the handheld device for the second dimension;
      calculate a first path length from the first acceleration plot using a first integration procedure;
      calculate a second path length from the second acceleration plot using a second integration procedure, wherein said first integration procedure or second integration procedure comprising:
         (i) identifying a start point of the movement and an end point of the movement; and
         (ii) integrating between the start point of the movement and the end point of the movement, to find the path length; and
      calculate a final path length based on the first path length and the second path length.

24. The handheld electronic device of claim 23, said first or second integration procedure causing the processor to:
   compute a set of velocity plots by integrating the acceleration plot over a set of integration intervals, wherein the integration intervals have a decreasing span and exclude a growing initial portion of the acceleration plot;
   compute a set of distances by integrating the set of velocity plots; and
   estimate the path length based on the set of computed distances.

25. The handheld electronic device of claim 23, said first or second integration procedure causing the processor to:
   identify the start and end point of the movement; and
   integrate between the start and end points of the movement to find the path length.

26. A measuring module for a handheld electronic device, the measuring module configured to measure a path length and comprising:
   a user interface to receive user input indicative of a starting and an ending of a translation movement of the handheld electronic device over the path;
   a data receiver unit configured to obtain from a plurality of acceleration sensors a first acceleration plot of the handheld device for a first dimension and a second acceleration plot of the handheld device for a second dimension, the acceleration plots being indicative of an acceleration of the handheld electronic device while the handheld electronic device is translated over the path for the first dimension and an acceleration of the handheld electronic device for the second dimension;
   a data processing unit configured to:
      calculate a first path length from the first acceleration plot using a first integration procedure;
      calculate a second path length from the second acceleration plot using a second integration procedure, wherein said first integration procedure or second integration procedure comprising:
         (i) identifying a start point of the movement and an end point of the movement; and
         (ii) integrating between the start point of the movement and the end point of the movement, to find the path length; and calculate a final path length based on the first path length and the second path length; and an output unit configured to output the calculated final path length to a user.

27. The measuring module of claim 26, said first or second integration procedure causing the data processing unit to:

compute a set of velocity plots by integrating the acceleration plot over a set of integration intervals, wherein the integration intervals have a decreasing span and exclude a growing initial portion of the acceleration plot;

compute a set of distances by integrating the set of velocity plots; and estimate the path length based on the set of computed distances.

28. The measuring module of claim 26, said first or second integration procedure causing the data processing unit to:

identify the start and end point of the movement; and integrate between the start and end points of the movement to find the path length.

29. The method according to claim 1, wherein the first integration procedure and the second integration procedure are the same integration procedure.

30. The non-transitory computer-readable media storing computer-readable instructions according to claim 21, wherein the first integration procedure and the second integration procedure are the same integration procedure.

31. The handheld electronic device according to claim 23, wherein the first integration procedure and the second integration procedure are the same integration procedure.

\* \* \* \* \*